US006981998B2

(12) United States Patent
Dermeik et al.

(10) Patent No.: US 6,981,998 B2
(45) Date of Patent: Jan. 3, 2006

(54) FLAME-RETARDANT COMPOSITIONS OF METHANEPHOSPHONIC ACID, BORIC ACID AND AN ORGANIC BASE

(75) Inventors: Salman Dermeik, Augsburg (DE); Reinhold Braun, Schwabmünchen (DE); Karl-Heinz Lemmer, Augsburg (DE)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 10/495,677

(22) PCT Filed: Nov. 12, 2002

(86) PCT No.: PCT/EP02/12602

§ 371 (c)(1),
(2), (4) Date: May 13, 2004

(87) PCT Pub. No.: WO03/042329

PCT Pub. Date: May 22, 2003

(65) Prior Publication Data

US 2005/0017222 A1 Jan. 27, 2005

(30) Foreign Application Priority Data

Nov. 15, 2001 (EP) .................................. 01127098

(51) Int. Cl.
*D06M 13/44* (2006.01)

(52) U.S. Cl. .................................... 106/18.13; 252/608

(58) Field of Classification Search ............. 106/18.13; 252/608

See application file for complete search history.

(56) References Cited

U.S. PATENT DOCUMENTS

| 4,452,849 A | 6/1984 | Nachbur et al. ............. 428/264 |
| 4,666,967 A | 5/1987 | Richardson et al. ........ 524/130 |
| 5,156,775 A * | 10/1992 | Blount ........................ 252/609 |
| 6,054,515 A * | 4/2000 | Blount ........................ 524/118 |
| 6,156,240 A * | 12/2000 | Blount ........................ 252/601 |

FOREIGN PATENT DOCUMENTS

| DE | 4140966 | 6/1993 |
| EP | 0469339 | 2/1992 |
| EP | 0499867 | 8/1992 |

OTHER PUBLICATIONS

Chem. Abstr. 118:23705 for EP 0499867 (1992).
English language abstract for EP 0469339 (1992).
Chem. Abstr. 120:56637 for DE 4140966 (1993).

* cited by examiner

*Primary Examiner*—Matthew A. Thexton
(74) *Attorney, Agent, or Firm*—Kevin T. Mansfield

(57) ABSTRACT

Compositions are described that are obtainable by preparing a mixture of methanephosphonic acid, boric acid, water and optionally urea and subsequently adding dicyandiamide and/or guanylurea to this mixture. The compositions thus obtained are useful for conferring a flame-retardant finish on fibrous materials, especially on woven fabrics composed of cellulosic fibers.

10 Claims, No Drawings

FLAME-RETARDANT COMPOSITIONS OF METHANEPHOSPHONIC ACID, BORIC ACID AND AN ORGANIC BASE

This invention relates to compositions obtainable by adding dicyandiamide and/or guanylurea and also optionally, in addition, urea to a mixture which includes methanephosphonic acid, boric acid and water and also optionally urea. This invention further relates to the use of such compositions for conferring a flame-retardant finish on fibrous materials, especially on textile fabrics.

It is known to confer flame-retardant properties on textile fabrics by treating the fabrics with compositions which include boric acid. This is known for example from DE-A 41 40 966. It is also known to obtain a flame-retardant finish by means of compositions which include a salt of methanephosphonic acid and guanylurea. This is described in EP-B 57 668 and U.S. Pat. No. 4,666,967. EP-A 499 867 discloses compositions which include formaldehyde reaction products of the salts of methanephosphonic acid and guanylurea.

EP-A 469 339 describes compositions which include modified salts of methanephosphonic acid and guanylurea and additionally boric acid. The modification of the salts takes the form of a reaction with formaldehyde, ie a methylolation, having been carried out. These compositions have the disadvantage that they still include free formaldehyde and that formaldehyde can become detached in the course of use. It would therefore be desirable to provide compositions which include boric acid and salts of methanephosphonic acid and guanylurea such that these salts do not include formaldehyde either in free or in bound form. However, tests have shown that an aqueous solution of such salts can have only very small amounts of boric acid added to it. On addition of larger amounts of $H_3BO_3$, the stability/homogeneity of the resulting compositions deteriorates, as a result of which these compositions have only limited usefulness, if any, for conferring a flame-retardant finish on textiles by customary methods.

It is an object of the present invention to provide aqueous compositions which have excellent stability and include salts of methanephosphonic acid and guanylurea, these salts not including bound formaldehyde and the good stability of the compositions being extant even when the compositions include substantial amounts of boric acid.

By "substantial amounts" of boric acid are meant amounts which lead to the compositions becoming instable when these amounts of boric acid are added to a ready-produced solution of a salt of methanephosphonic acid and guanylurea.

This object is achieved by a composition obtainable by the following successive steps of:
a) preparing a mixture A), which includes methanephosphonic acid, boric acid and water,
b) adding dicyandiamide and/or guanylurea to said mixture A),
c) optionally neutralizing the resultant mix with a base.

Compositions according to the invention have the following advantages:
1. They have excellent stability even when including amounts of boric acid which would lead to instable compositions when these amounts of boric acid were added subsequently to an aqueous solution of a salt of methanephosphonic acid and guanylurea. True, compositions according to the invention cannot include infinitely large amounts of $H_3BO_3$ without the stability/homogeneity of the compositions being adversely affected. But it is possible for boric acid to be included in an up to 10 times larger amount than in the case of the subsequent addition of boric acid to the ready-prepared aqueous solution of the salt. It is believed that this advantage of using a larger amount of $H_3BO_3$ is the result of the boric acid being mixed with methanephosphonic acid before the addition of dicyandiamide and/or guanylurea takes place.
2. They are very useful for conferring a flame-retardant finish on fibrous materials, especially on textiles which include cellulosic fibers, eg cotton. The flame-retardant properties thereby conferred on the textiles can be at least equivalent to and in many cases even superior to those in the case of the use of compositions which are free of boric acid but otherwise include the same components in the same amounts as compositions according to the invention. The many times better flame-retardant effect is possibly attributable to a synergism between the phosphorus/nitrogen compounds and the boron compound. Thus it becomes possible for prior art aqueous solutions of salts of methanephosphonic acid and guanylurea to have a portion of these salts replaced by boric acid and so obtain a cost advantage as well as other benefits.

It is a decisive criterion of compositions according to the present invention that methanephosphonic acid is mixed with water and boric acid (and optionally urea) to form the abovementioned "mixture A)" before any addition of dicyandiamide and/or guanylurea takes place.

Compositions according to the present invention are obtainable by preparing in a first step (=step a)) a mixture (=mixture A)) which includes methanephosphonic acid, boric acid and water and in a second step (=step b)) heating this mixture A) to a temperature in the range from 50° C. to 130° C. and preferably from 70° C. to 95° C. and at this temperature adding dicyandiamide and/or guanylurea to the mixture A). There can optionally be a subsequent third step (=step c)) in which the mix formed is neutralized with a base. Further components can optionally be added during or after step c) has been carried out.

Mixture A) can be prepared in process step a) by adding boric acid in solid form a little at a time to an aqueous solution of methanephosphonic acid ($CH_3PO(OH)_2$) and, where appropriate, stirring the resulting mixture until a clear solution has formed. To raise the rate of dissolution, elevated temperature can be employed.

In a preferred embodiment, the aqueous solution of methanephosphonic acid is prepared by adding water and a catalyst, for example phosphoric acid or sulfuric acid, preferably methanephosphonic acid (catalyst for the subsequent hydrolysis), to dimethyl methanephosphonate or to monomethyl methanephosphonate or to a mixture of these esters, and then heating the resulting mixture, preferably to a temperature in the range from 120° C. to 180° C. and adding water a little at a time at this temperature, the temperature being maintained in the range mentioned until substantially complete hydrolysis of the ester groups to methanephosphonic acid has taken place.

During the hydrolysis and subsequently thereto, the methanol formed and a portion of the water are distilled off. Then, if desired after the hydrolysis product has been cooled down, sufficient water is added for the desired mixing ratio of methanephosphonic acid:water to be present in mixture A) after boric acid has been added. The cooled aqueous solution of methanephosphonic acid can be used direct, without further purifying operations, for preparing the mixture A).

It is advantageous for the mixture A) to include urea as well as methanephosphonic acid, water and boric acid. Aside from these 4 components it preferably does not include any further ingredients with the exception of small non-hydrolyzed residual amounts of monomethyl or dimethyl methanephosphonate. The presence of urea in mixture A) is preferred because, as a result, the amount of dicyandiamide and/or guanylurea which is added in step b) can be kept lower than in the case where mixture A) includes no urea. The urea can be added to the aqueous solution which includes methanephosphonic acid before the addition of boric acid or at the same time or after the addition of boric acid. Instead of adding urea before step b) is carried out, the urea can also be added simultaneously or after addition of dicyandiamide and/or guanylurea. However, this embodiment is less preferable, mixture A) including no urea in this case.

The first step of preparing mixture A) is preferably carried out using such amounts of starting materials that the resulting mixture A) includes 25 to 50 parts by weight of methanephosphonic acid per 100 parts by weight of water and 0.1 mol to 0.3 mol of boric acid per mole of methanephosphonic acid.

Where mixture A) is prepared using urea in addition, it is preferable to use such amounts of urea that the mixture A) includes 2 to 10 g of urea per 100 g of methanephosphonic acid.

In the second step (=step b)) for preparing compositions according to the present invention, either dicyandiamide ($H_2N$—C(=NH)—NH—C≡N) or guanylurea ($H_2N$—C(=NH)—NH—$CONH_2$) or a mixture of these two bases is added to the mixture A). For this purpose, the mixture A) is preferably heated beforehand to a temperature in the range from 70° C. to 95° C. and it is at this temperature that dicyandiamide and/or guanylurea are added. During this addition, which is preferably carried out a little at a time, the reaction mixture is preferably maintained at a temperature in the range from 70° C. to 95° C.

Process step b) is preferably carried out by adding only dicyandiamide to the mixture A). However, instead of dicyandiamide it is also possible to use guanylurea or a mixture of dicyandiamide and guanylurea. When dicyandiamide is used, it can be added to the mixture A) in solid form, preferably a little at a time. In aqueous solution, dicyandiamide hydrolyzes to guanylurea, so that an aqueous solution is obtained after the step b) has ended that includes a guanylurea salt of methanephosphonic acid as well as other ingredients.

In a preferred embodiment of the process for preparing compositions according to the present invention, no guanylurea is used in said step b) and in that 20 to 30 g of dicyandiamide are used per 100 g of said mixture A).

When guanylurea or a mixture of dicyandiamide and guanylurea is used in step b), it is preferable to use such amounts of these compounds that as many equivalents of basic nitrogen atoms are present per 100 g of mixture A) as in the case where only dicyandiamide is used in an amount of 20 to 30 g per 100 g of mixture A).

Process step b) may optionally be followed by a process step c), especially when the product mixture obtained after step b) has a pH (at 20° C.) of less than 3.5. This process step comprises neutralizing the base. Useful bases include amines, for example triethanolamine. The pH obtained after neutralization is preferably in the range from 3.3 to 4.5.

During or after neutralization (step c)) the compositions according to the present invention may have added to them further components which are known to one skilled in the art of textile finishing, for example cellulose crosslinkers and/or oil- or water-repellent products such as polysiloxanes or fluoropolymers. It will be appreciated that these further components can also be added after process step b) where no process step c) is carried out.

Compositions according to the present invention are very useful for conferring a flame-retardant finish on fibrous materials, especially on textile fabrics. They are particularly useful for finishing woven fabrics which are 50 to 100% by weight cellulosic fiber, for example woven cotton fabrics. From 0 to 50% by weight may here be composed of other fibers, for example synthetic fibers. But it is also possible to obtain good flame-retardant properties on textile fabrics which are 50 to 100% by weight synthetic fiber, for example polyester. The finished textile fabrics can be processed into flame-retardant textiles, for example industrial fabrics or home textiles such as upholstery fabrics.

The compositions according to the invention can be applied to the textile fabrics by methods which are known to one skilled in the art of textile finishing. It is preferable to employ a pad-mangling process for this, in which case the compositions according to the invention may where appropriate be diluted to use concentrations customary for pad-mangling processes. Pad-mangling is followed by drying and optionally curing at elevated temperatures by likewise known methods.

The examples which follow illustrate the invention.

EXAMPLE 1

Preparation of an Aqueous Solution of Methanephosohonic Acid 491 g of dimethyl methanephosphonate, 156 g of methanephosphonic acid and 13 g of water were heated to 140° C. 330 g of water were then added over 17 hours in such a way that the internal temperature was 135° to 140° C. throughout the entire water addition period. At the same time, methanol-water mix and some methanephosphonic ester were distilled off. This was followed by stirring at 140° C. for 90 minutes, cooling to about 85° C. and the addition of a further 830 g of water during the cooling phase. The methanephosphonic acid solution obtained was about 35% in strength and virtually free of methyl and dimethyl methanephosphonates (disregarding traces of residual amounts).

EXAMPLE 2

Not Inventive

To 406 g of the aqueous methanephosphonic acid solution obtained in example 1 were added 115 g of solid dicyandiamide a little at a time at 85° C. This was followed by stirring at 85° C. for 5 hours. After cooling to 50° C., 35 g of water were then added. When the temperature of the solution was about 40° C., 17 g of triethanolamine were added. This gave a clear solution (= "solution A") whose pH at room temperature was about 3.5.

EXAMPLE 3

Inventive

To 406 g of the hot aqueous methanephosphonic acid solution at 85° C. obtained according to example 1 were added 23 g of boric acid in solid form. The mixture was stirred at 85° C. until a clear solution was present. The rest of the procedure was as in example 2, starting with the addition of dicyandiamide. This gave a clear solution (="solution B") having a pH of about 3.5 at room temperature.

EXAMPLE 4

Inventive

To 406 g of the aqueous methanephosphonic acid solution obtained according to example 1 were added 4 g of urea in solid form and 23 g of boric acid at 85° C. The mixture was stirred at 85° C. until a clear solution was present. The rest of the procedure was as in example 2, starting with the addition of dicyandiamide; however, only 110 g of dicyandiamide were added instead of 115 g. This gave a clear solution (="solution C") having a pH of about 3.5 at room temperature.

Table 1 below shows the stabilities of the solutions A, B and C.

TABLE 1

|  | Storage temperature | | | |
| --- | --- | --- | --- | --- |
|  | +60° C. | −20° C. | −10° C. | 0° |
| Solution A | 19 | 14 | 12 | 12 |
| Solution B | 19 | 19 | 19 | 19 |
| Solution C | 39 | 25 | 19 | 24 |

When stored at room temperature, all the solutions were stable and homogeneous for several months. Table 1 indicates the number of days in the course of which the solutions began to become instable, i.e. where deposits started to be formed. It is to be noted that the inventive solutions B and C are superior in stability to the comparative solution A.

EXAMPLE 5

Finishing Tests

The solutions A, B and C were used to finish woven undyed 100% cotton fabrics by pad-mangling.

Liquor concentrations: 180 g of solution per l of liquor in all cases

Following padding, the fabrics were mangled off to a wet pick-up of about 80% (based on fabric weight before padding) and dried at 110° C. for 10 min. The finished fabrics were subsequently tested for flame-retardant properties. The test was carried out according to DIN 54 336 (November 1986 issue), using a flaming time of 3 sec.

The results are shown in table 2 (lower numerical values are better than higher numerical values).

TABLE 2

|  | Burning time (sec) | Length burned (mm) |
| --- | --- | --- |
| Solution A | 7 | 85 |
| Solution B | 0 | 20 |
| Solution C | 0 | 20 |

These results show that the flame-retardant effects obtained with solution B and with solution C are superior to those obtainable with solution A.

What is claimed is:

1. A composition obtained by the following successive steps of:
   a) preparing a mixture A), which includes methanephosphonic acid, boric acid and water,
   b) adding dicyandiamide and/or guanylurea to said mixture A),
   c) optionally neutralizing the resultant mix with a base.

2. A composition as claimed in claim 1, wherein said mixture A) is heated to a temperature in the range from 70° C. to 95° C. after said step a) has been carried out and wherein step b) is carried out in said range from 70° C. to 95° C.

3. A composition as claimed in claim 1, wherein said methanephosphonic acid used in said step a) was prepared by hydrolysis of mono- and/or dimethyl methanephosphonate.

4. A composition as claimed in claim 1, wherein said mixture A) includes 25 to 50 parts by weight of methanephosphonic acid per 100 parts by weight of water and 0.1 mol to 0.3 mol of boric acid per mole of methanephosphonic acid.

5. A composition as claimed in claim 1, wherein no guanylurea is used in said step b) and wherein 20 to 30 g of dicyandiamide are used per 100 g of said mixture A).

6. A composition as claimed in claim 1, wherein said mixture A) additionally includes urea.

7. A composition as claimed in claim 6, wherein said mixture A) includes 2 to 10 g of urea per 100 g of methanephosphonic acid.

8. A method of treating fibrous materials which comprises applying a composition as claimed in claim 1 thereto.

9. The method as claimed in claim 8, wherein said fibrous materials are wovens which are 50 to 100% by weight cellulosic fiber.

10. The method as claimed in claim 8, wherein said fibrous materials are textile fabrics.

* * * * *